United States Patent [19]

Fischer

[11] Plant 5,190

[45] Feb. 14, 1984

[54] AFRICAN VIOLET PLANT

[75] Inventor: Arnold Fischer, Hanover, Fed. Rep. of Germany

[73] Assignee: Pan American Plant Company, Parrish, Fla.

[21] Appl. No.: 390,641

[22] Filed: Jun. 21, 1982

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet cultivar known by the cultivar name Ice Palace and having profuse, relatively large star-shaped flowers which form a massive bouquet carried on erect peduncles above the foliage.

3 Drawing Figures

The present invention comprises a new and distinct cultivar of African violet plant, botanically known as Saintpualia hybrids, and hereinafter referred to by the cultivar name Ice Palace.

The new cultivar was referred to during the breeding and selection process by the designation V7-H29-W, and is a product of a planned breeding program. The basic objective of the breeding program was to create a new African violet cultivar having a profusion of white single star-shaped, actinomorphic rotate flowers positioned on erect peduncles well above the foliage.

The new cultivar was originated from a cross made in a controlled breeding program in Hanover, West Germany. Both the female and male parents are unknown at this time.

Ice Palace was discovered and selected by me as a flowering plant within the progeny of the stated cross in a controlled environment in Fallbrook, Calif. Asexual reproduction of the new cultivar by leaf cuttings, as initially performed by me at Fallbrook, Calif., with subsequent propagations at Chicago, Ill., and Parrish, Fla., have demonstrated that the combination of characteristics as herein disclosed for the new cultivar are firmly fixed and are retained through successive generations of asexual reproduction.

Ice Palace has not been observed under all possible environmental conditions. The phenotype may vary significantly with variations in environment such as temperature, light intensity and day length. The following observations, measurements and values describe the new cultivar as grown in greenhouse conditions which closely approximate those generally used in commercial practice.

The following traits have been repeatedly observed and are determined to be basic characteristics of Ice Palace, which in combination distinguish this African violet as a new and distinct cultivar:

1. Pure white, very large single star-shaped flowers.
2. The flowers are carried by numerous strong and erect peduncles thereby providing a massive bouquet positioned above the foliage which provides an attractive contrast.
3. The cultivar can be finished in approximately 10–12 weeks from a 2¼" plantlet.
4. An abundance of foliage and vigorous growth habit.

The accompanying photographic drawings show a typical specimen plant, or components thereof, of the new cultivar. Sheet 1 comprises a perspective view of Ice Palace, principally the massive bouquet of white flowers. Also appearing on Sheet 1 is an enlarged top view of the flower, with the tinging (pink) around the center of the flower being more apparent. Sheet 2 comprises a photograph showing the underside of typical foliage at various stages of development or taken from different parts of the plant.

In the following description, color references are made to The Royal Horticultural Society Colour Chart (RHS), except where general colors of ordinary significance are referred to. The perspective view of the cultivar was taken under indirect, natural lighting conditions.

Botanical classification: Saintpaulia hybrids, cv. Ice Palace.

Parentage:

*Male parent.*—Unknown.

*Female parent.*—Unknown.

Propagation: The new cultivar holds its distinguishing characteristics through successive propagations by leaf cuttings.

Plant: From 8–15 cm. when fully grown in pots; generally rosette in shape, and vigorous growth habit, with an abundance of foliage.

*Leaves.*—General form: Cordate, with repand margin. Diameter: 5–7 cm. wide and 5–8 cm. long. Texture: Glossy. Veins: Pinnate. Color (Upperside): 147A. (Underside): 147D.

*Flowers.*—Buds: Approximately 1 cm. in diameter and length, generally rounded in shape, with normal rate of opening; color of petals when first dividing, 145C; color of petals when unfurling 145C. Sepals: 5 in number, lanceolate in shape and branched, with sepals standing up when flowers open; Color: Inside 145A, color outside 145A. Phyllaries: Two in number, shape lanceolate. Calyx: Generally funnel-shaped and relatively small, splits, hairy. Peduncle: 11–15 cm. in length, when fully grown, hairy, erect and slender, color 145A.

*Individual flowers.*—Size: Very large, 4–4.5 cm. in diameter, 1 cm. in depth. Color: Upperside: 155D, with pink 56D tinging at the center on certain flowers. Underside: 155D. Borne: In generally cup-shaped clusters on upright peduncles 11–15 cm. in length. Five petals arranged sympetalously. Shape: Star, actinomorphic rotate, margin ruffled, apex rounded, soft texture and satin appearance, with the petals becoming more flat as the bloom matures. Flowering habits: Blooms profusely and intermittently year round; individual blooms last approximately 2–3 weeks and persist to drying up.

*Reproductive organs.*—Stamens: Five in number, arranged singly around the ovary, anthers basifixed. Anthers: 2–3 mm. in size. Filaments: 3 mm. in length, color light yellow. Pollen color: Yellow. Pistils: One in number, styles 5–8 mm. in length, color 55D. Ovaries: Superior.

*Disease resistance.*—No diseases noted to date.

*General observations.*—Ice Palace is a profusely flowering cultivar having large white single star-shaped flowers which are held on erect peduncles above the relatively light green foliage, thereby providing an attractive appearance and contrast.

I claim:

1. A new and distinct cultivar of African violet known by the cultivar name Ice Palace, as described and illustrated, and particularly characterized by its profuse flowering, and relatively large white single star-shaped flowers positioned on erect peduncles above the foliage.

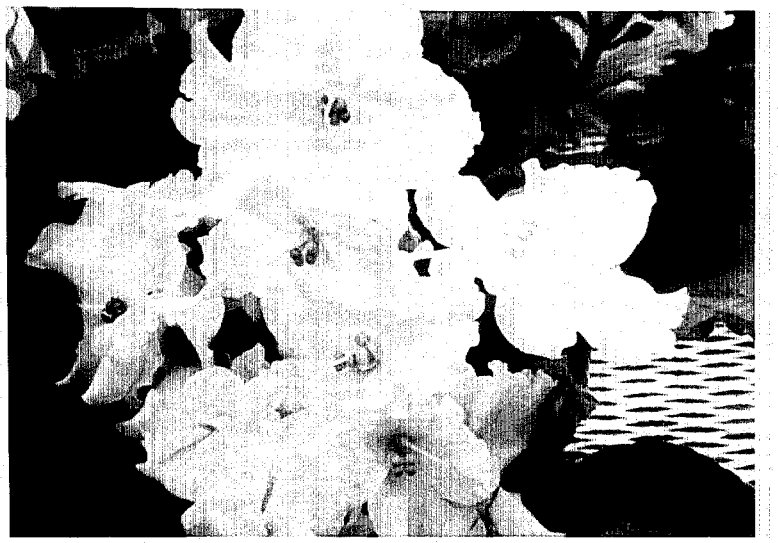
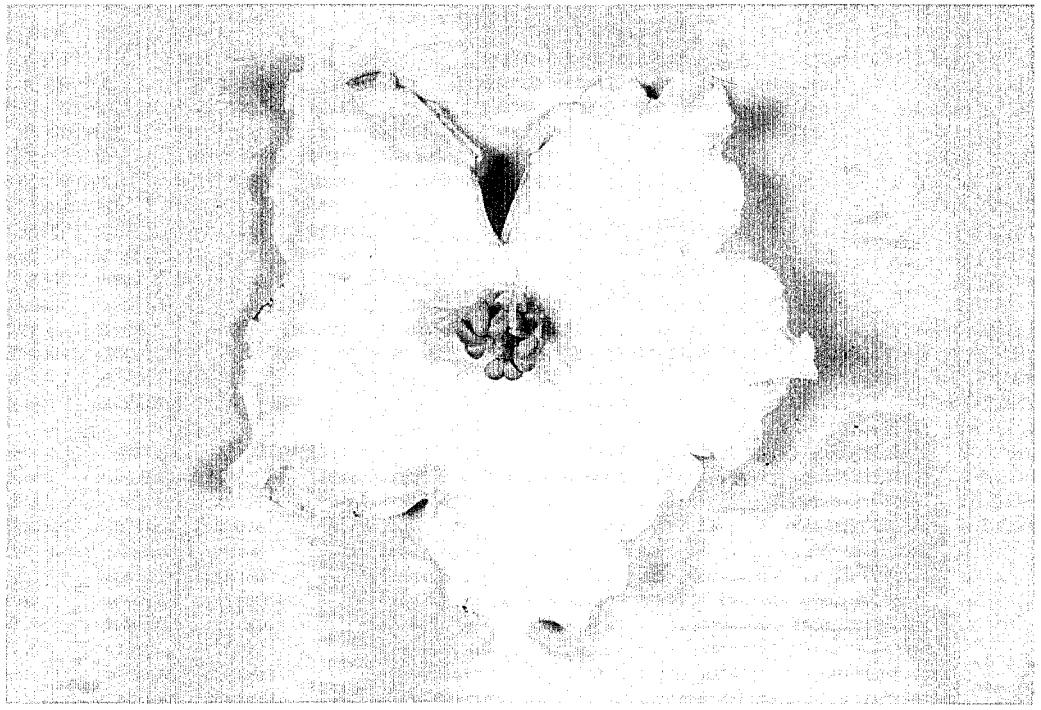

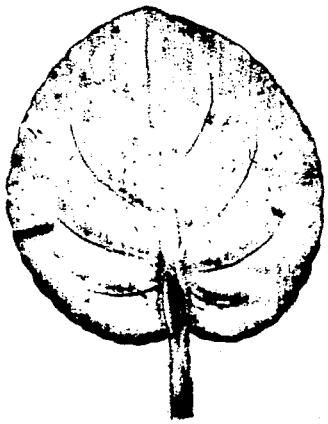
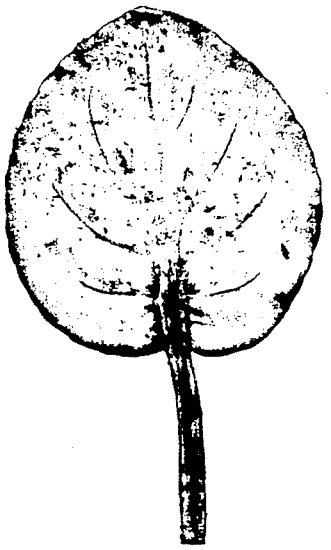
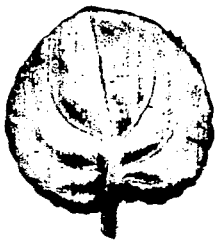
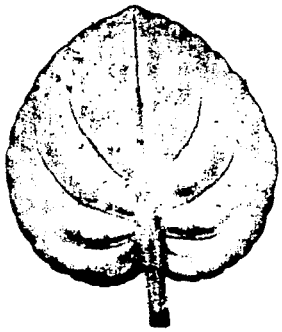

* * * * *